United States Patent [19]
McClain

[11] Patent Number: 5,372,132
[45] Date of Patent: Dec. 13, 1994

[54] SENSOR POSITIONING AID AND METHOD

[75] Inventor: John McClain, Cardiff, Calif.

[73] Assignee: Biomagnetic Technologies, Inc., San Diego, Calif.

[21] Appl. No.: 911,977

[22] Filed: Jul. 9, 1992

[51] Int. Cl.⁵ .......................... A61B 5/00; A61B 5/05; G01R 33/02
[52] U.S. Cl. ....................... 128/630; 128/653.001; 324/248
[58] Field of Search ............... 128/630, 653.1, 653.2, 128/653.5, 662.03, 663.01, 632, 635, 639, 897; 434/289; 324/248

[56] References Cited

U.S. PATENT DOCUMENTS

| | | | |
|---|---|---|---|
| D. 88,727 | 12/1932 | Metzner | 434/289 |
| 2,402,194 | 6/1946 | Wolfe | 434/289 |
| 4,793,355 | 12/1988 | Crum et al. | 128/653.1 |
| 4,899,753 | 2/1990 | Inoue et al. | 128/639 |
| 5,026,287 | 6/1991 | Yamada | 434/289 |
| 5,070,861 | 12/1991 | Einars et al. | 128/653.1 |
| 5,094,243 | 3/1992 | Puy et al. | 128/662.03 |

Primary Examiner—Lee S. Cohen
Assistant Examiner—Marianne Parker
Attorney, Agent, or Firm—Gregory Garmong

[57] ABSTRACT

A sensor positioning aid includes a concavely curved transparent dish having a shape congruent with a lower surface of a sensor, and locating means on the dish for establishing external reference positions in relation to the dish. The locating means preferably includes a rim around the dish and markings on the dish. The positioning aid is placed at a selected location on the head, and the sensor is aligned to the head by aligning it to the rim of the positioning aid. The positioning aid is removed, and the head translated in relation to the sensor to place it closely adjacent to the sensor, without reorienting the sensor. The placement aid is removed and measurements are taken using the sensor. If necessary, the sensor is thereafter reoriented by reference to the markings.

20 Claims, 2 Drawing Sheets

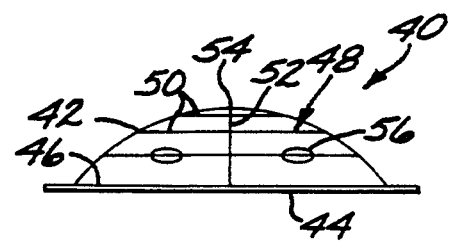
FIG.4
FIG.5
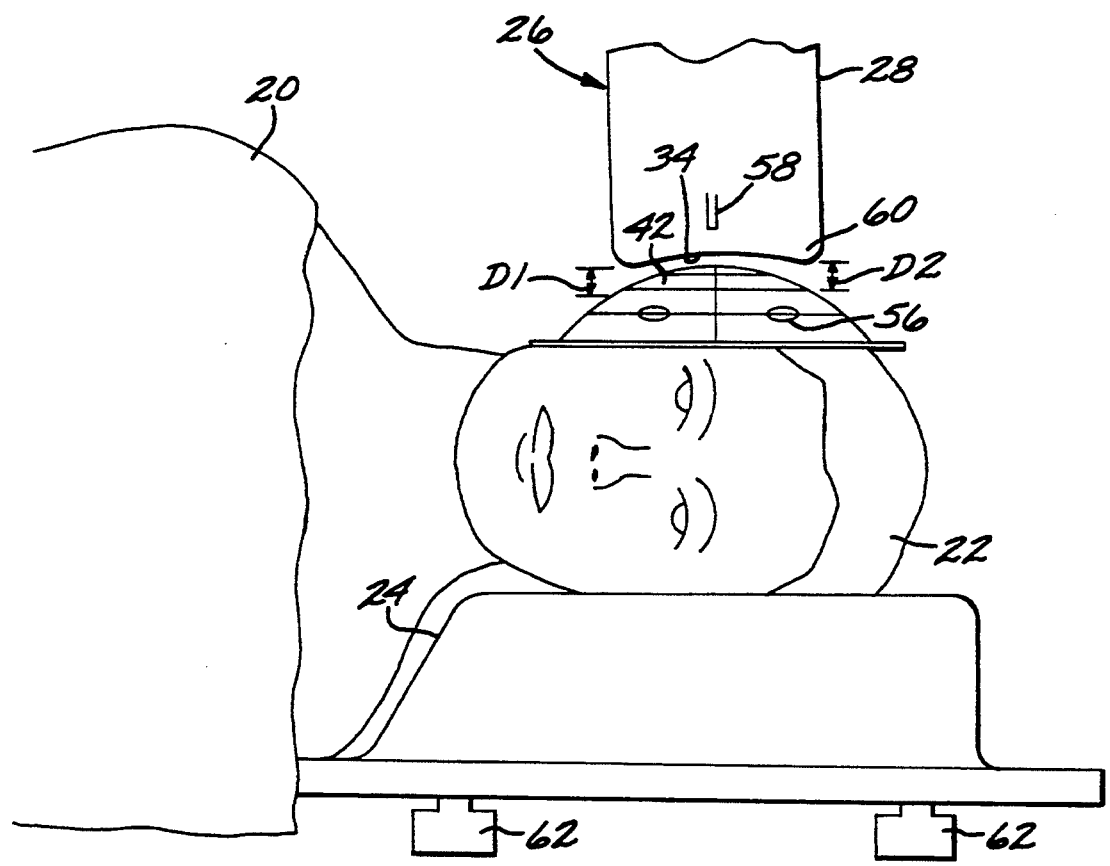

SENSOR POSITIONING AID AND METHOD

BACKGROUND OF THE INVENTION

This invention relates to the positioning of biomeasurement sensors close to the body of a subject, and, more particularly, to the accurate positioning of a biomagnetometer dewar tail adjacent to the body of a human subject.

The biomagnetometer is a device for measuring small magnetic fluxes that are produced by a living subject. Small electric currents flowing in the body produce magnetic fields, and the biomagnetic fields are detected by input coils connected to detect the biomagnetometer. The biomagnetic fields are typically on the order of one ten-millionth of the magnitude of the earth's magnetic field, requiring the use of very sensitive detectors, special shielding, and sophisticated electronic signal processing.

The most sensitive detector available, a superconducting quantum interference device ("SQUID"), is operated at superconducting temperatures, 10K or less for the most sensitive of such SQUIDs. The SQUIDs must therefore be contained within a device that maintains such low temperatures. In the most commonly used practice today, the pickup coils and SQUIDs are placed into a dewar vessel and cooled with a cryogenic fluid such as liquid helium.

The dewar is supported from a gantry or stand placed adjacent to the subject. The support structure must be sturdy, inasmuch as current-generation biomagnetometer dewars are typically about 4 feet long, 18 inches in maximum diameter, and 200 pounds in weight when loaded with cryogenic fluid.

The support structure must also be readily operable by hospital technicians to position the dewar precisely and accurately at a selected location near the subject. Once the dewar is positioned, it must remain stably locked at that position. It also must be easily and precisely repositioned, as initial measurements may indicate the need to move the instrument only a few centimeters.

The magnetic fields produced by a subject are very small in magnitude, and their intensities decrease rapidly with increasing distance from the region of the body producing the field. The dewars are therefore typically designed with a reduced section, tubular dewar tail extending from the main body of the dewar. The lower surface of the dewar tail is generally shaped to fit the contours of the human head, with specific dimensions selected based upon a statistical survey of head shapes and sizes. The pickup coils and detectors are contained at the bottom of the dewar tail, so that they may be placed very close to the subject's head in an accurate manner. Where the dewar contains multiple pickup coils and detectors, as is usually the case, it is desirable to position the pickup coils in a preselected arrangement with comparable pickup coils equally spaced from the region of the subject being measured. The various pickup coils can therefore detect the magnetic fields most efficiently to produce a mapping of those magnetic fields, from which the characteristics of the sources within the head may be inferred.

Hospital technicians expend a great deal off time in each instance attaining a precise positioning of the biomagnetometer dewar tail. It is difficult to position a tubular dewar tail precisely adjacent to the human head, and then reposition it precisely at another location if that is required by the initial results. The dewar and gantry are counterweighted, but are still difficult to move in a precise manner. Moreover, the patients may be sensitive to contact by the dewar, and care must be taken to avoiding such contact.

A number of different dewar positioning techniques are used or have been proposed. In one, the technician positions and repositions the dewar based upon his Judgment, an approach that lacks reproducibility and precision. In another, various electronic techniques using lasers, proximity sensors, or other sophisticated tools have been proposed. These techniques may be operable, but add significantly to the cost of the biomagnetometer and may be unreliable. Moreover, most types of electronic devices must be specially engineered to remove any trace of a remnant magnetic field after they are turned off, as such fields may interfere with the biomagnetic measurements. In a third approach, conventional positioning methods used for other types of medically related equipment have been tried. In many instances, the positioning techniques seem to work well for positioning a device at a distance of a foot or more from the body, but do not work well when they are used in an attempt to position the dewar reproducibly to within a few tenths of an inch or less of the subject.

There has been proposed no simple, reliable technique for precisely positioning a heavy object such as a dewar tail closely adjacent to a subject. Such a technique would desirably permit quick, reliable, reproducible initial positioning and repositioning as necessary. The present invention fulfills this need, and further provides related advantages.

SUMMARY OF THE INVENTION

The present invention provides a positioning aid and technique for its use in precisely positioning large sensors closely adjacent to the body of a subject. The approach of the invention is inexpensive and does not interfere with the taking of data from weak sources. The method is readily utilized by operators with minimal training, and permits reproducible positioning and repositioning of the sensor to within a few tenths of an inch.

In accordance with the invention, a positioning aid for use in positioning a sensor closely adjacent to the human body comprises a concavely curved transparent dish having a shape congruent with a lower surface of a sensor, and locating means on the dish for establishing external reference positions in relation to the dish. In a preferred approach, the dish is made of transparent acrylic. The preferred dish is shaped as a segment of a sphere.

The locating means preferably includes two elements of structure designed to permit the user to position the sensor. The first is a rim extending around the periphery of the dish, and the second is a set of markings on the dish. The markings include a set of concentric circles marked on the dish, concentric with the rim. Radial lines, distances, angles, and the locations of sensor elements relative to the dish can also be marked.

The invention also extends to the technique for using the positioning aid. In accordance with this aspect of the invention, a method for locating a sensor closely adjacent the human body comprises furnishing a sensor positioning aid of the type discussed, placing the positioning aid at a location on the human body selected for measurement, and aligning a sensor in relation to the locating means. The preferred rim portion of the locating means permits the sensor to be positioned very precisely by inspection, particularly where the end of the sensor is slightly concave. After the sensor is aligned, the positioning aid is preferably removed and the subject is moved slightly, if necessary, to place the selected location immediately adjacent to the sensor, without reorienting the sensor.

The sensor instrument is then operated in the usual manner. It may later become necessary to reorient the sensor because, for example, the initial measurements indicate that slightly altered positioning would yield better results. In that case, the sensor is moved away from the subject, the positioning aid is replaced, and the sensor is reoriented using the markings of the locating means as a guide. The positioning aid is removed, the sensor is again brought to the desired position, and measuring resumes.

The approach of the invention has important advantages over prior techniques. It uses visual alignment, but in relation to a well defined article rather than the less-well-defined surface of the body of the subject. It does not require sophisticated electronic and other instrumentation, and is therefore reliable and inexpensive. The positioning aid produces no electromagnetic signal or residual field that might interfere with the taking of biomagnetic data. Other features and advantages of the invention will be apparent from the following more detailed description of the preferred embodiments, taken in conjunction with the accompanying drawings, which illustrate, by way of example, the principles of the invention.

BRIEF DESCRIPTION OF THE DRAWINGS

FIG. 4 is an elevational view of the sensor positioning aid of FIG. 2; and

FIG. 5 is a view similar to that of FIG. 1, except that the sensor positioning aid is used to orient the sensor.

DETAILED DESCRIPTION OF THE PREFERRED EMBODIMENT

Figure 1:
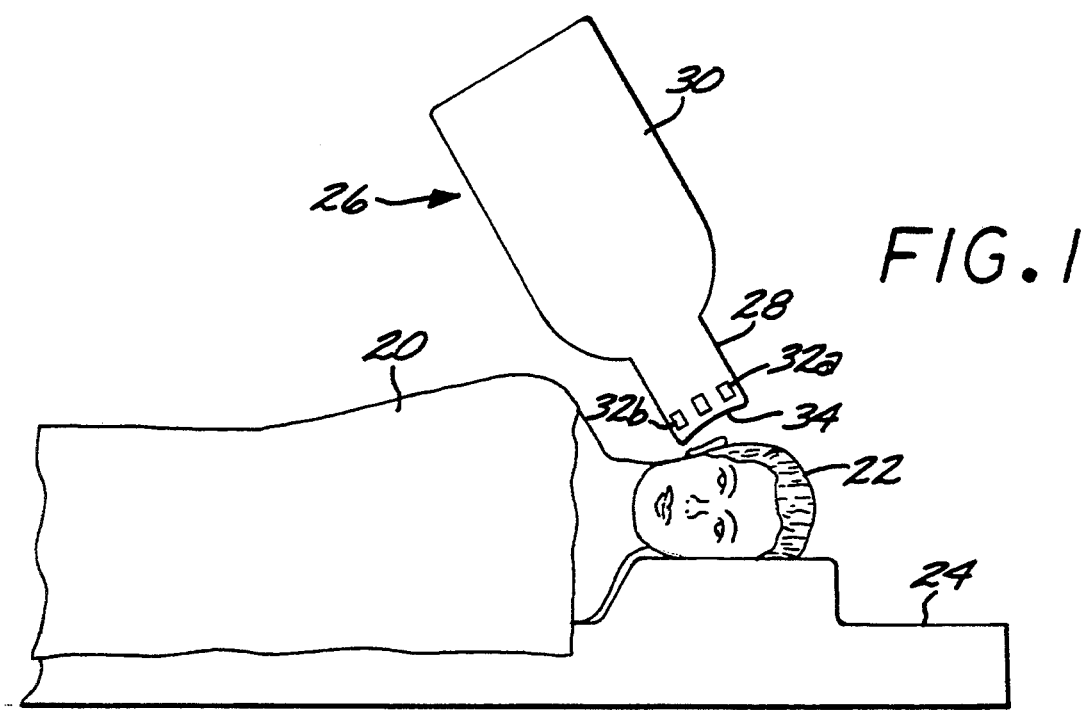
FIG. 1 is an elevational view, with portions broken away, of a sensor positioned adjacent a subject's head by visual inspection, without using the sensor positioning aid of the invention.

FIG. 1 depicts a human subject 20 whose head 22 rests upon a movable bed 24. A generally cylindrical dewar 26 is positioned closely adjacent to the subject's head 22. A tubular dewar tail 28 extends axially from a dewar body 30. Inasmuch as the application of most interest is in the field of biomagnetometry, the dewar tail 28 is shown to contain a number of biomagnetic pickup coils 32. (As used herein, the term "sensor" includes the dewar, dewar body, dewar tail, pickup coils, SQUIDs, related electronics, and interconnections that are provided as a single unit and are positioned adjacent the body.) The dewar tail 28 is tailored for use in measuring biomagnetic signals from the brain of the subject, and its lower end 34 is curved concavely to generally conform to the head 22 of the subject 20.

When the dewar tail 28 is positioned closely adjacent to the head 22, it is desirable that similarly positioned pickup coils be at least approximately equally spaced at as small a distance as possible from the subject's head. The magnitude of the magnetic field produced by brain functions within the head decreases rapidly with increasing distance from the head. If the dewar tail 28 is oriented at an angle to the head, as shown in FIG. 1, some pickup coils such as the pickup coil 32a will be unnecessarily spaced farther from the head 22 than the otherwise equivalently placed pickup coil 32b. The pickup coil 32a will therefore sample a magnetic field that is unnecessarily diminished by excessive distance from the head. Great care is taken to build dewar tails having thin walls in the lower end of the dewar tail in order to place the pickup coils very near the object being measured. Improper placement of the dewar can completely negate much of this effort.

It would seem at first glance to be an easy matter to position the dewar 26 and thence the pickup coils 32 properly. In practice, however, hospital technicians spend a great deal of time positioning the dewar in what appears, by inspection, to be the proper orientation in relation to the portion of the body being measured. It is particularly difficult to orient the dewar if the subject's head is not shaved. The technician cannot see the skin surface of a person whose hair remains, and the varying character and style of the hair makes it difficult and unreliable to guess the position of the dewar end 34 relative to the skin surface.

Figure 2:
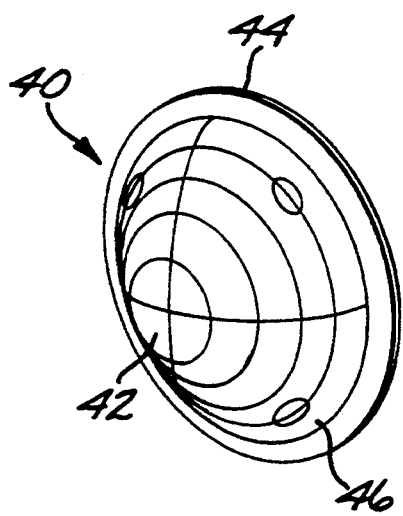
FIG. 2 is a perspective view of a sensor positioning aid.
Figure 3:
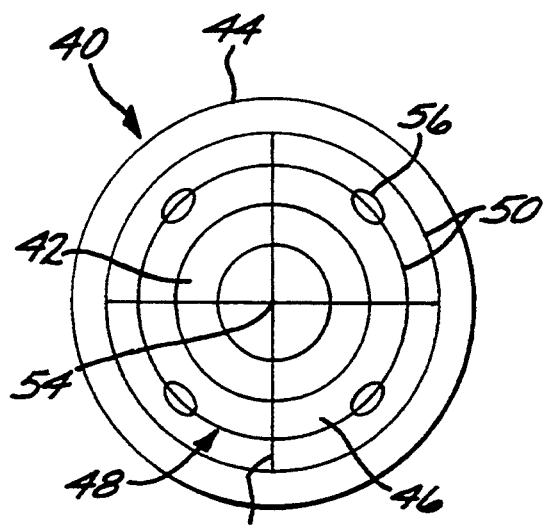
FIG. 3 is a plan view of the sensor positioning aid of FIG. 2.

FIGS. 2–4 illustrate a positioning aid 40 used to improve the precision and reproducibility of the positioning of the sensor dewar 30 in relation to the body of the subject, in this case the head 22. The positioning aid 40 is formed with a concavely curved dish 42. The concave curvature is shaped to fit to be congruent with the lower surface 34 of the dewar tail 28. That is, the shape of the surface of the dish 42 is the same as that of the lower surface 34 of the dewar tail 28. In one embodiment, the lower surface 34 is approximately a segment of a sphere, and therefore the dish 42 is also shaped as a segment of a sphere. Its surface is on the locus of points approximately equidistant from a point, but is not a complete or even the majority of a sphere. In this usage, some deviation from a perfect segment of a sphere is permitted within the term "segment of a sphere".

Making the lower surface 34 and the dish 42 a segment of a sphere provides the positioning aid 40 with good symmetry and permits it to be easily rotated about its central axis of symmetry. For positioning a sensor adjacent to the head, as shown in the present drawings, the dish of the positioning aid 40 is placed comfortably against the subject's head. The fit typically is not exact, as any particular location on the human head is not likely to match exactly to the fixed shape of the lower surface 34 of the dewar tail 28. Even with a slightly imperfect fit, however, the positioning aid 40 permits the lower surface 34 of the sensor 28 to be reproducibly positioned adjacent to the subject's head. The dish is preferably made from a clear, transparent material, such as acrylic plastic.

The positioning aid 40 is further provided with at least one, and desirably at least two, types of locating means for establishing exterior reference positions for the lower surface of the dewar tail 28 in relation to the positioning aid. One type of positioning aid is a rim 44 extending around a periphery 46 of the dish 42. The rim 44 is preferably made of the same material as the dish 42 for easy fabrication in one piece. The rim 44 aids in achieving an accurate, reproducible positioning of the dewar tail 28 relative to the head 22, in the manner to be described subsequently.

A second type of locating means is markings 48 placed onto the dish 42, as can be seen best in FIGS. 3 and 4. Three types of markings 48 have been found useful in performing positioning and repositioning of the dewar 26 in relation to the head 22, using the positioning aid 40. The first is a series of concentric rings 50, that are concentric with the periphery 46 of the dish 42 and the rim 44. The rings 50 are desirably spaced apart by a known distance, such as 2 centimeters between each pair of rings, and are so marked.

A second type of marking is radial lines 52 extending from a center 54 of the dish (about which the rings 50 are concentric when viewed in the plan view of FIG. 3). The radial lines 52 are preferably spaced by an angular spacing of 90 degrees around the circumference of the dish 42.

A third type of marking is generally elliptical location indicators 56 for the positioning of the pickup coils 32 of the dewar tail 28. That is, if one of the location indicators 56 is aligned with the known circumferential positioning of one of the pickup coils 32, then the other location indicators 56 indicate the locations of the other pickup coils that are shown. The marking can be accomplished, for example, by rotating the positioning aid 40 about the center 54 of the dish 42 to align a specific location indicator 56 (e.g., the location indicator for a specific pickup coil) with a mark on the exterior of the dewar tail 28, as shown for a mark 58 and a specific location indicator 56 in FIG. 5.

The use of the positioning aid 40 is illustrated in FIG. 5 for the case of positioning the dewar tail 28 closely adjacent to the head of the subject. The dish 42 of the positioning aid 40 is placed over a portion of the head 22. In the illustration, the subject 20 lies on the bed 24 on his or her side. The dish 42 is placed over the side of the head. Since the dish is transparent, the location of primary interest may be viewed through the dish, and the location of interest aligned with the center 54 of the dish 42. This portion of the alignment is most easily accomplished with the dewar 26 removed. The dish 42 fits generally against the head 22 of the subject 20 and is pressed gently against the head sufficiently to negate irregularities due to the presence of hair or the shape of the subject's skull.

The dewar tail 28 is brought into position above the head 22, as shown in FIG. 5. The angular position of the dewar tail 28 is varied so that the shortest distance from a periphery 60 of the dewar tail 28 to the rim 44 is the same around the entire circumference of the positioning aid 40. That is, as shown in FIG. 5, the distance D1 from periphery 60 to rim 44 is the same as the distance D2 from periphery 60 to rim 44 at another location around the circumference. This distance is checked either by eye or with a ruler or other standard. Since the distance D is typically only a few millimeters or less, the alignment is accomplished accurately even with no more than a visual sighting. The rim 44 gives a well defined locus from which the distance to the dewar tail 28 can be measured.

Once alignment of the dewar to the head is complete, the positioning aid 40 can remain in place, or, preferably, is removed. The distance from the head to the pickup coils may then be reduced by raising the bed 24 using a lifting system, such as a series of hydraulic jacks 62. (Equivalently, the dewar 26 can be lowered, while retaining its angular orientation unchanged.) The head can be placed arbitrarily close to the end of the dewar tail, or in contact with it.

The pickup coils and detectors are operated in the normal manner to gather data.

It sometimes occurs that, after some data is taken, the technician or researcher may observe that even better data could be obtained by moving the pickup coils to another position. Moreover, it is often possible from the first set of data to quantify that movement in an approximate manner. For example, the data might suggest moving the pickup coil array 5 centimeters in a direction away from the location of a particular pickup coil. The markings 48 are used cooperatively to accomplish the repositioning. First, the bed 24 is lowered (or the dewar raised) sufficiently to permit the positioning aid 40 to be reinserted to its original location. The location of location indicator 56 for the particular sensor of interest is found. The required direction and amount of movement of the dewar tail 28 are identified in the frame of reference of the markings 48. The positioning aid 40 is moved by these amounts so that the center 54 of the dish 42 is at the new desired location. Finally, the dewar 25 is moved to realign it to the positioning aid in the manner previously discussed for the initial positioning.

Experience using the positioning aid with an actual biomagnetometer having a 48 inch long, 18 inch diameter, 200 pound dewar has shown that precise positioning and repositioning are easily accomplished using this tool, typically in 1-2 minutes. Previously, positioning and repositioning by estimation was a tedious operation, often requiring 10 minutes or more and even then yielding results far less certain and reproducible than with the present approach.

Although particular embodiments of the invention have been described in detail for purposes of illustration, various modifications may be made without departing from the spirit and scope of the invention. Accordingly, the invention is not to be limited except as by the appended claims.

What is claimed is:

1. A positioning system, comprising:
   a sensor having an end surface thereon; and
   a transparent dish having a shape congruent with the end surface of the sensor.

2. The positioning system of claim 1, wherein the dish is made of acrylic plastic.

3. The positioning system of claim 1, wherein the dish is shaped as a segment of a sphere.

4. A positioning system, comprising:
   a sensor having a surface thereon;
   a dish having a shape congruent with the surface of the sensor; and
   locating means on the dish for establishing external reference positions in relation to the dish, wherein the locating means includes a rim extending around the periphery of the dish.

5. A positioning system, comprising:
   a sensor having a surface thereon;
   a dish having a shape congruent with the surface of the sensor; and
   locating means on the dish for establishing external reference positions in relation to the dish, wherein the locating means includes a set of markings on the dish.

6. A positioning system, comprising:
   a sensor having a surface thereon;
   a dish having a shape congruent with the surface of the sensor; and
   locating means on the dish for establishing external reference positions in relation to the dish, wherein the locating means includes a set of concentric circles marked on the dish.

7. A positioning system, comprising:
a sensor having a surface thereon;
a transparent dish shaped to conform to the surface of sensor;
a rim extending around the periphery of the dish; and
a set of markings on the dish.

8. The positioning system of claim 7, wherein the set of markings includes a set of concentric circles.

9. The positioning system of claim 7, wherein the sensor has a pickup coil therein, and wherein the set of markings includes an indication of the location of the pickup coil within the sensor.

10. The positioning aid of claim 7, wherein the transparent dish is shaped as a segment of a sphere.

11. A method for locating a sensor closely adjacent to a human body, the method comprising the steps of:
furnishing a sensor having an end surface thereof;
furnishing a sensor positioning aid, the positioning aid including a dish having a shape congruent with the end surface of the sensor;
placing the positioning aid at a location on the human body selected for measurement; and thereafter aligning the sensor at an orientation in relation to the sensor positioning aid.

12. The method of claim 11, including the additional step, after the step of aligning, of
removing the positioning aid.

13. The method of claim 12, including the additional step, after the step of removing, of
moving the human body in relation to the sensor to place the selected location immediately adjacent the sensor, without reorienting the sensor.

14. The method of claim 12, including the additional step, after the step of removing, of
later replacing the positioning aid, and
reorienting the sensor in relation to the positioning aid by reference to the set of markings.

15. The method of claim 11, wherein the step of furnishing a sensor positioning aid includes the step of furnishing a positioning aid including locating means having
a rim extending around the periphery of the dish, and
a set of markings including a set of circles concentric with the rim.

16. The method of claim 11, wherein the step of furnishing a sensor positioning aid includes the step of furnishing a positioning aid whose dish is shaped as a segment of a sphere.

17. The method of claim 11, wherein the step of furnishing a sensor positioning aid includes the step of furnishing a positioning aid whose dish is transparent.

18. The method of claim 11, wherein the step of furnishing a sensor positioning aid includes the step of furnishing a positioning aid whose dish further includes marking means thereon for establishing the relationship of the sensor to the dish.

19. The method of claim 11, wherein the step of furnishing a sensor includes the step of furnishing a sensor having a pickup coil therein, and wherein the step of furnishing a sensor positioning aid includes the step of furnishing a positioning aid whose dish further includes marking means thereon for establishing the relationship of the pickup coil within the sensor to the dish.

20. The method of claim 11, wherein the step of furnishing a sensor positioning aid includes the step of furnishing a positioning aid whose dish further includes a rim thereon.

* * * * *